(12) United States Patent
Golden

(10) Patent No.: US 8,668,683 B2
(45) Date of Patent: Mar. 11, 2014

(54) URINARY CATHETER COLLECTION SYSTEM

(75) Inventor: John H. Golden, Greensboro, GA (US)

(73) Assignee: Medical Technologies of Georgia, Inc., Covington, GA (US)

( * ) Notice: Subject to any disclaimer, the term of this patent is extended or adjusted under 35 U.S.C. 154(b) by 669 days.

(21) Appl. No.: 12/029,291

(22) Filed: Feb. 11, 2008

(65) Prior Publication Data

US 2009/0204106 A1    Aug. 13, 2009

(51) Int. Cl.
*A61M 27/00* (2006.01)

(52) U.S. Cl.
USPC ........... 604/544; 604/327; 604/328; 604/329; 604/330; 604/331; 604/346; 604/348; 604/349; 604/350; 604/351; 604/352; 604/353; 604/354; 604/317; 604/318; 604/319; 604/320; 604/321; 604/322; 604/323; 604/324; 604/325; 604/326; 604/192; 604/364

(58) Field of Classification Search
USPC .......................................... 604/544, 327–331
See application file for complete search history.

(56) References Cited

U.S. PATENT DOCUMENTS

| | | |
|---|---|---|
| 3,854,483 A | 12/1974 | Powers |
| 4,062,363 A | 12/1977 | Bonner, Jr. |
| 5,147,341 A | 9/1992 | Starke et al. |
| 5,226,530 A | 7/1993 | Golden |
| 6,004,305 A | 12/1999 | Hursman et al. |
| 6,053,905 A | 4/2000 | Daignault, Jr. et al. |
| 6,602,224 B1 | 8/2003 | Simhambhatla |
| 6,887,230 B2 * | 5/2005 | Kubalak et al. ............... 604/544 |

* cited by examiner

*Primary Examiner* — Tatyana Zalukaeva
*Assistant Examiner* — Ilya Treyger
(74) *Attorney, Agent, or Firm* — FisherBroyles; Anthony J. DoVale

(57) ABSTRACT

The present invention relates to a urinary catheter collection system comprising a urinary catheter, a collection bag neck, and a collection bag body. The invention particularly relates to a urinary catheter collection system having a detachable bag body, which allows a user the option to detach the collection bag body from the collection bag neck so that urine may drain from the catheter into a suitable container, such as a toilet, preventing the user from having to empty or dispose of a used urine collection bag body.

17 Claims, 5 Drawing Sheets

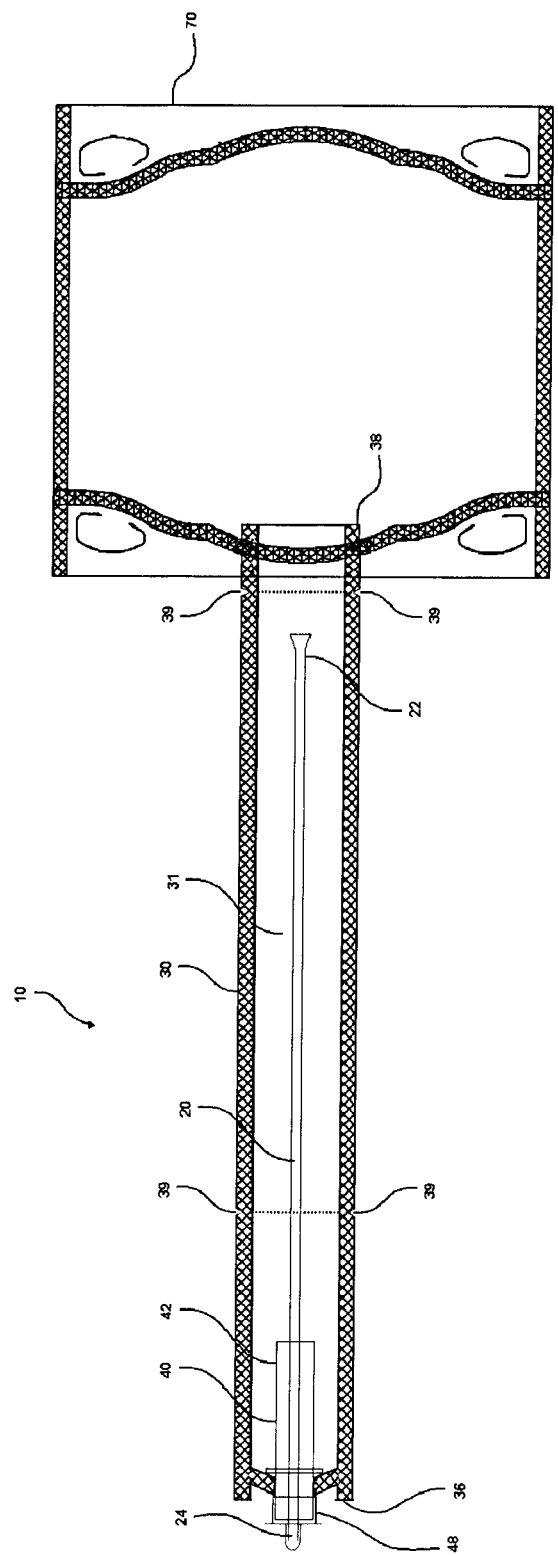
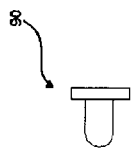
FIG. 1
FIG. 2

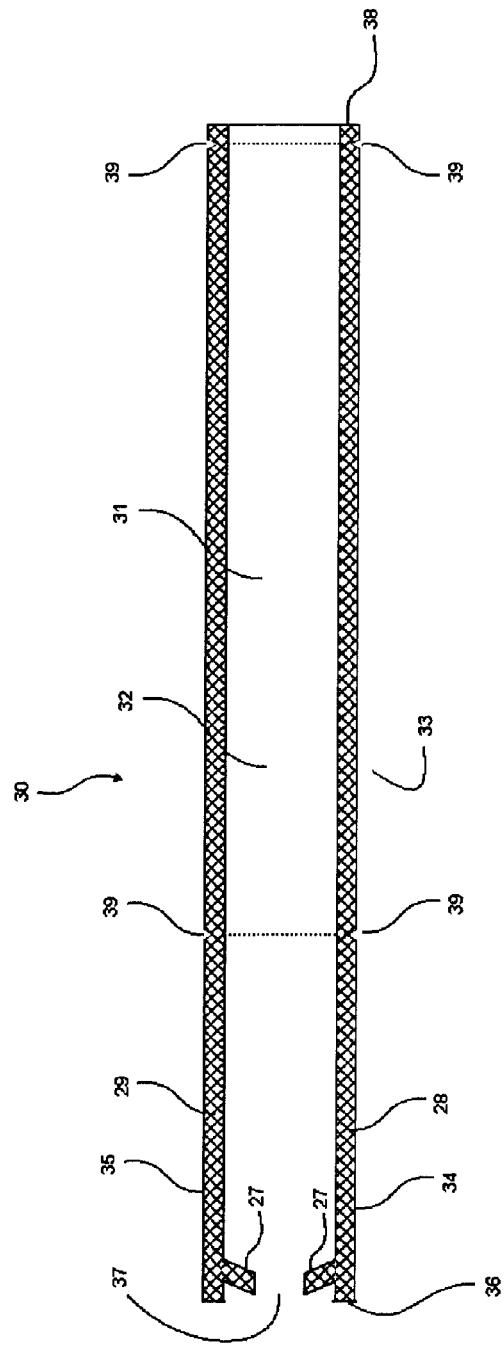

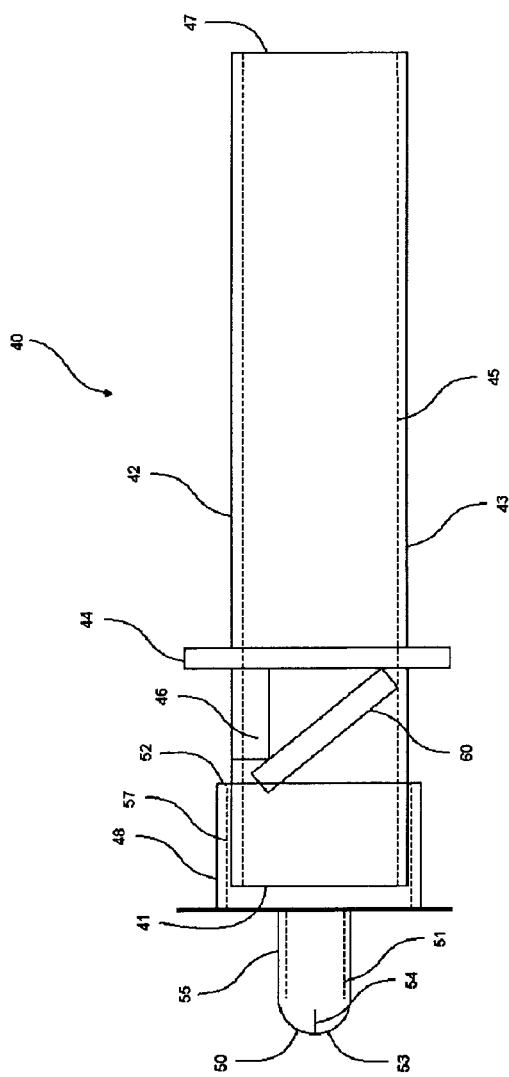
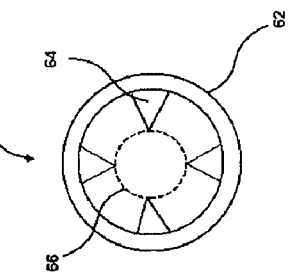
FIG. 6
FIG. 4
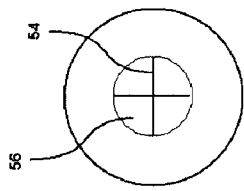
FIG. 5

URINARY CATHETER COLLECTION SYSTEM

BACKGROUND OF THE INVENTION

1. Field of the Invention

The present invention relates to a urinary catheter collection system for use with a urinary catheter. Particularly, the invention relates to a urinary catheter collection system that enables the user to determine the method of disposal of the urine.

2. Description of the Related Art

A wide variety of catheters are available for insertion into the body for introduction or withdrawal of fluids. Urinary catheters are flexible tubes designed to drain urine from the bladder by insertion into the urethra. They are packaged in sterile containers and may be lubricated for insertion prior to packaging or prior to use. Intermittent urinary catheters are designed to be inserted for each use and are commonly used by patients who are either able to catheterize themselves or have the function performed by a caregiver. One type of intermittent catheter comprises a urinary catheter pouch, which also serves as the sterile package for the catheter. See, for example, U.S. Pat. No. 3,854,483 to Powers, U.S. Pat. No. 5,226,530 to Golden, U.S. Pat. No. 6,004,305 to Hursman et al, U.S. Pat. No. 5,147,341 to Starke et al and U.S. Pat. No. 6,053,905 to Daignault et al. Another type of catheter is an intermittent catheter contained in a conduit pouch, whereby the pouch may be opened and used to transfer urine to a toilet or a urine collection container.

Catheterization is accomplished by introducing the proximal tip of a catheter into the urethra, and then "longitudinally collapsing and extending the pouch in an accordion-like manner until the tip reaches the bladder" as described in U.S. Pat. No. 6,602,224 to Kavanagh and U.S. Pat. No. 4,062,363 to Bonner. When the catheter is in use, urine flows through the catheter into the catheter pouch, where it is collected. After the user has finished the use of the catheter, he may either empty the contents of the catheter pouch into a toilet or a urine collection container for disposal, or he may close the pouch and dispose of it at a later time.

However, when emptying the bag of urine into a suitable container, it is possible for the user to spill urine onto the clothes, which may be embarrassing for the user. Another potential issue is possible leakage from the closed pouch during transportation in the patient's backpack or storage sleeve prior to disposal.

Accordingly, it would be useful to have a catheter system in which a catheterized user may elect to allow urine to flow from a catheter through a collection bag neck into a collection bag, or in certain situations, to remove the collection bag so that urine will flow from the catheter through the elongate collection bag neck and into a receptacle, such as a toilet.

SUMMARY OF THE INVENTION

The present invention provides a urinary catheter collection system with a urinary catheter that is at least partially disposed therein a collection bag neck that is in sealed fluid communication with a collection bag body. The invention particularly relates to a urinary catheter collection system comprising a selectively detachable urine collection bag body. The invention allows a catheterized user to choose to either collect urine in the collection bag body and eventually dispose of it or to quickly and easily detach the collection bag body from the collection bag neck and directly empty the bladder into a commode or other disposal vessel via the collection bag neck. Most users would prefer to empty their bladder directly into a commode and this invention allows them to do that. However, if a commode isn't available at the time of urgency, the user may void into the attached collection bag body and empty the contents at a more convenient time.

The urinary catheter collection system comprises a urinary catheter having a longitudinal axis and an inner diameter, configured for insertion through a user's urethra into the bladder to allow urine to be dispelled. The invention further comprises an elongate collection bag neck having a longitudinal axis, a distal end and a proximal end, and defining a longitudinally extending catheter tube pathway configured for storing of the catheter. The invention further comprises a collection bag body having a volume for collecting urine from the catheter. The catheter, collection bag neck, and collection bag body are in sealed fluid communication with each other.

In one aspect, the elongate collection bag neck has at least one perforation formed in an edge on the elongate collection bag neck. The perforation extends through at most a portion of an edge seal, and is configured to allow the elongate collection bag neck to be easily torn manually by the user. In this aspect, at least a portion of the elongate collection bag neck may be removed from collection bag body, so that the user of the set is not required to collect urine in the collection bag body and may elect to void directly through the collection bag neck into a commode or other receptacle.

In another aspect, the urinary catheter collection system of the present invention further comprises a guide housing having a proximal end and a distal end, wherein the guide housing is fixedly attached to the proximal end of the elongate collection bag neck and defines a longitudinally extending catheter pathway. The guide housing is configured to allow a user to selectively slide the catheter longitudinally therethrough the catheter pathway of the guide housing in a first direction external of the elongate collection bag neck. A retaining ring located in the guide housing may be used to prevent the catheter from sliding in a second direction along its longitudinal axis into the elongate collection bag neck.

These and other objects of the present invention will be clear when taken in view of the detailed specification and disclosure in conjunction with the appended Figs.

BRIEF DESCRIPTION OF THE DRAWINGS

The accompanying drawings, which are incorporated in and constitute a part of this specification, illustrate certain aspects of the instant invention and together with the description, serve to explain, without limitation, the principles of the invention. Like reference characters used therein indicate like parts throughout the several drawings.

FIG. 1 is a top view of one embodiment of a urinary catheter collection system of the present invention showing a catheter, a collection bag body, a collection bag neck, and a guide housing.

FIG. 2 is a top view of a protective cap of the catheter collection system of FIG. 1.

FIG. 3 is a top view of the elongate collection bag neck of FIG. 1.

FIG. 4 is a partially transparent top view of the guide housing of FIG. 1 showing a sleeve, an introducer tip, a protective cap, and a retaining ring.

FIG. 5 is an elevational view of the introducer tip of FIG. 4.

FIG. 6 is an elevational view of the retaining ring of FIG. 4.

DETAILED DESCRIPTION OF THE INVENTION

Figure 7:
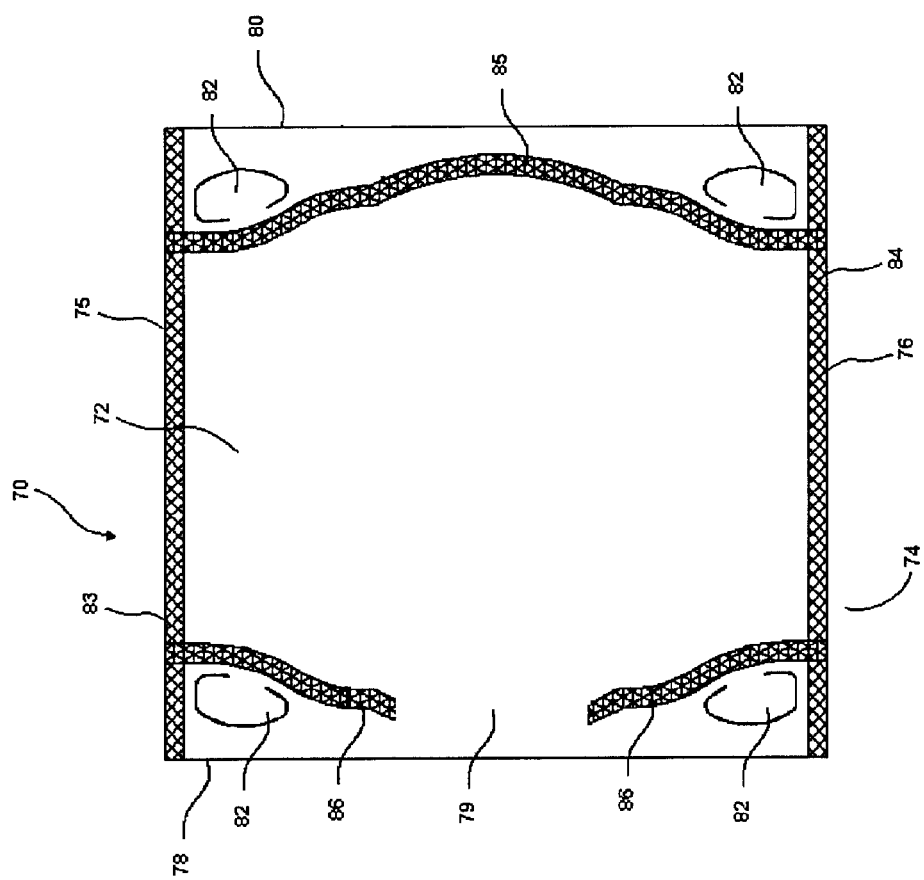
FIG. 7 is a top view of the collection bag of FIG. 1.

The present invention may be understood more readily by reference to the following detailed description of the invention and the Examples included therein and to the Figs and their previous and following description.

Before the present systems, articles, devices, and/or methods are disclosed and described, it is to be understood that this invention is not limited to specific systems, specific devices, or to particular methodology, as such may, of course, vary. It is also to be understood that the terminology used herein is for the purpose of describing particular embodiments only and is not intended to be limiting.

The following description of the invention is provided as an enabling teaching of the invention in its best, currently known embodiment. To this end, those skilled in the relevant art will recognize and appreciate that many changes may be made to the various aspects of the invention described herein, while still obtaining the beneficial results of the present invention. It will also be apparent that some of the desired benefits of the present invention may be obtained by selecting some of the features of the present invention without utilizing other features. Accordingly, those who work in the art will recognize that many modifications and adaptations to the present invention are possible and may even be desirable in certain circumstances and are a part of the present invention. Thus, the following description is provided as illustrative of the principles of the present invention and not in limitation thereof.

As used in the specification and the appended claims, the singular forms "a," "an" and "the" include plural referents unless the context clearly dictates otherwise. Thus, for example, reference to "a catheter movement control device" includes two or more such devices, and the like.

Ranges may be expressed herein as from "about" one particular value, and/or to "about" another particular value. When such a range is expressed, another embodiment includes from the one particular value and/or to the other particular value. Similarly, when values are expressed as approximations, by use of the antecedent "about," it will be understood that the particular value forms another embodiment. It will be further understood that the endpoints of each of the ranges are significant both in relation to the other endpoint, and independently of the other endpoint. It is also understood that there are a number of values disclosed herein, and that each value is also herein disclosed as "about" that particular value in addition to the value itself. For example, if the value "10" is disclosed, then "about 10" is also disclosed. It is also understood that when a value is disclosed that "less than or equal to" the value, "greater than or equal to the value" and possible ranges between values are also disclosed, as appropriately understood by the skilled artisan. For example, if the value "10" is disclosed the "less than or equal to 10" as well as "greater than or equal to 10" is also disclosed. It is also understood that throughout the application, data is provided in a number of different formats and that this data represents endpoints and starting points, and ranges for any combination of the data points. For example, if a particular data point "10" and a particular data point 15 are disclosed, it is understood that greater than, greater than or equal to, less than, less than or equal to, and equal to 10 and 15 are considered disclosed as well as between 10 and 15. It is also understood that each unit between two particular units are also disclosed. For example, if 10 and 15 are disclosed, then 11, 12, 13, and 14 are also disclosed.

"Optional" or "optionally" means that the subsequently described event or circumstance may or may not occur, and that the description includes instances where said event or circumstance occurs and instances where it does not.

The present invention relates to a urinary catheter collection system for use with a urinary catheter, comprising an elongate collection bag neck, and a collection bag body. The invention particularly relates to a urinary catheter collection system having a detachable collection bag body, which allows a user the option to detach the collection bag body from the catheter collection system so that urine may drain from the catheter into a suitable container, such as a toilet, preventing the user from having to empty or dispose of a used urine collection bag.

As illustrated in FIGS. 1 and 2, in one aspect, the urinary catheter collection system 10 may comprise a catheter 20, a collection bag neck 30, a collection bag body 70, and a guide housing 40.

The catheter 20 may be an elongate tube formed of soft, thermoplastic material. In one aspect, the distal end of the catheter may be frustoconically shaped, to prevent the catheter from being removed from the elongate collection bag neck. In another aspect, the catheter may be coated with a lubricant to allow for easier insertion of the catheter into the urethra.

In one aspect, the elongate collection bag neck 30 defines an elongate neck conduit, which may be formed of a thermoplastic film. The thermoplastic film of the elongate collection bag neck may be substantially transparent or substantially opaque. In another aspect, the elongate collection bag neck is approximately the same length as the catheter, although other lengths are contemplated. The elongate collection bag neck may serve as a protective covering for maintaining the catheter 20 in sterile condition prior to use, and as a conduit for urine to reach the collection bag body 70 or as a conduit for urine to reach a suitable container. FIG. 3 illustrates the elongate collection bag neck, which has a first wall 32, a second wall 33, longitudinal edges 34 and 35, proximal end 36 and distal end 38. In one aspect, the elongate collection bag neck may be formed by sealing the first wall to the second wall along the longitudinal edges 34, 35 by sealing techniques as are commonly known in the art, for example, heat-sealing or radio frequency (RF) welding, to form longitudinal edge seals 28, 29. Proximal end 36 of the elongate collection bag neck 30 may be at most partially sealed by a proximal end seal 27, so that an opening 37 remains in the proximal end of the elongate collection bag neck 30. In another aspect, this opening may have a diameter that is substantially similar to the outer diameter 43 of the guide housing sleeve 42, described below. The distal end 38 of the elongate collection bag neck may be left unsealed so that the elongate collection bag neck forms a neck conduit 31.

In another aspect, also illustrated in FIG. 3, the elongate collection bag neck may have at least one perforation 39 formed in the sealed longitudinal edges 34, 35. The at least one perforation may be located at any location along the longitudinal length of the elongate collection bag neck 30. In one aspect, the perforation is located in an intermediate portion of the elongate collection bag neck, such that, when torn, the elongate collection bag neck is substantially bisected in a direction substantially transverse to its longitudinal axis. As one skilled in the art may appreciate, the at least one perforation 39 may extend from the edge of the first and second walls 32, 33 inwardly towards the center of the collection bag neck through at most a portion of the longitudinal seal, so that the interior of the collection bag neck conduit 31 formed by the elongate collection bag neck is not penetrated until the perforation is torn by the user. In another aspect, the at least one perforation may also be located at a distal end portion 38 of the elongate collection bag neck. The at least one perforation 39 is configured to provide a starting point for a user of the urinary catheter collection system 10 or a health care provider to manually tear the first wall and second wall of the collection bag neck, separating the distal end 38 of the elongate collection bag neck 30 from the proximal end 36, and thus, the collection bag body from proximal portion of the elongate collection bag neck.

The guide housing 40, illustrated in FIG. 4, may comprise a tubular sleeve 42 and an introducer tip 48. The sleeve may be formed of thermoplastic material having a proximal end 41, a distal end 47, and an outer diameter 43 that is slightly smaller than the opening 37 in the proximal end 36 of the elongate collection bag neck. In another aspect, the sleeve 42 may have an inner diameter 45 larger than the outer diameter of the catheter 20, forming a catheter pathway. In yet another aspect, the sleeve may have a shoulder 44 protruding around the exterior circumference of the sleeve. The sleeve shoulder may have a diameter greater than the diameter of the opening 37 in the elongate collection bag neck. In still another aspect, the sleeve may have a male protrusion, such as, for example, a shoulder 46, extending inwardly into the interior of the sleeve. Additionally, there may be a protective cap 90 configured to substantially cover the introducer tip and prevent introduction of foreign matter into the system while not in use.

The introducer tip 48 of the guide housing may be formed of soft, polymeric material, such as silicone or other similar material. The introducer tip may have a proximal end 50 and a distal end 52. The proximal end of the introducer tip may have an inner diameter 51 that is slightly larger than the outer diameter of the catheter 20, so that a catheter protecting member 55 is formed. The catheter protecting member may have a rounded end wall 53 with a plurality of diametrically extending slits 54 defining radially inwardly tapering protective flaps 56, as shown in FIGS. 4 and 5. In a further aspect, the distal end 52 of the introducer tip 48 may have an inner diameter 57 that is slightly larger than the outer diameter 43 of the sleeve 42. In yet another aspect, the distal end of the introducer tip may have a longitudinal length that is substantially equal to the distance from the shoulder 44 of the sleeve 42 to the proximal end 41 of the sleeve. As one skilled in the art can appreciate, the purpose of the introducer tip is to introduce the catheter into the urethra past the point in the urethra of bacterial introduction, thus reducing the risk of bacteria being introduced into the bladder of the patient.

The guide housing 40 may further comprise a retaining ring 60. As illustrated in FIG. 6, the retaining ring may be formed of a thermoplastic material and may have an outer diameter 62 that is slightly smaller than the inner diameter 45 of the sleeve 42. There may be at least one male protrusion, such as, for example, at least one retaining tab 64, extending inwardly into the interior of the retaining ring defining a catheter pathway 66. The catheter pathway of the retaining ring may have substantially the same diameter as the outer diameter of the catheter 20.

The collection bag body 70 is illustrated in FIG. 7. In one aspect, the collection bag body is connected to the elongate collection bag neck such that its interior volume is in selective sealed fluid communication with the elongate collection bag neck. In another aspect, the collection bag body may comprise a pouch formed of a thermoplastic film. The thermoplastic film of the collection bag body may be substantially transparent or substantially opaque. In the embodiment illustrated in FIG. 7, the collection bag body is generally rectangular in outline with a first wall 72, a second wall 74, longitudinal edges 75 and 76, a proximal end 78, and a distal end 80. In one aspect, the collection bag body may be formed by sealing the first wall 72 to the second wall 74 along the longitudinal edges by sealing techniques as are commonly known in the art, for example, heat-sealing or RF welding, to form collection bag longitudinal edge seals 83, 84. The distal end of the collection bag body 70 may similarly be sealed between the longitudinal edges 75, 76 by a collection bag distal end seal 85, forming a pouch. In another aspect, the proximal end 78 of the collection bag body may be sealed in a similar manner along at least a portion of the proximal end by a proximal end seal 86, however, the collection bag proximal end seal may not extend along the entire length of the proximal end, so that an unsealed opening 79 remains in the proximal end 78 of the collection bag providing access to the interior of the bag 70. While a rectangular bag body is shown, that shape is not critical, and other shapes for the collection bag body may be used provided that a sealed bag is formed with a single bag opening 79.

In yet another aspect, also as illustrated in FIG. 7, at least one handling hole 82 may be formed through both walls of the collection bag body to facilitate handling of the bag and allow the user to insert a digit into one of the holes in order to facilitate draining the urine from the collection bag body. The seal 85 formed along the distal end 80 of the collection bag body may be offset from the edges of the first wall 72 and the second wall 74 so that the at least one handling hole 82 may be formed in the collection bag body 70 without destroying its ability to collect and store urine. In another aspect, the seal 86 formed along the proximal end 78 of the collection bag body 70 may be offset from the edges of the walls so that the at least one handling hole may be formed in the collection bag body without destroying its ability to collect and store urine. In yet another aspect, seals may be formed in other areas on the collection bag body, for example, diagonally across a corner of the bag 70, to seal off areas of the bag so that the at least one handling hole 82 may be formed.

In another aspect, one or both of the first and second walls of the collection bag body 70 may be provided with volume indicia to allow the volume of urine collected in the bag to be easily measured.

For example, to assemble a urinary catheter collection system 10 according to this invention, the tubular sleeve 42 of the guide housing 40 may be inserted into the distal end 38 of the elongate collection bag neck 30. The sleeve may be pushed through the elongate collection bag neck until the proximal end 41 of the sleeve protrudes from the opening 37 left in the proximal end 36 of the elongate collection bag neck when the shoulder 44 of the sleeve is adjacent the proximal end seal 27 of the elongate collection bag neck 30. The shoulder of the sleeve 42 may be on the interior of the opening in the collection bag neck, thereby preventing the sleeve from being removed out the opening in the elongate collection bag neck, as the shoulder of the sleeve has a greater diameter than the opening 37 in the proximal end of the elongate collection bag neck. The opening 37 has a diameter that is substantially similar to the outer diameter 43 of the sleeve, so that the sleeve is held in place protruding from the proximal end of the elongate collection bag neck.

The proximal end 24 of the catheter 20 may be inserted through the distal end of the elongate collection bag neck 30 and through the tubular sleeve 42 of the guide housing, until the proximal end of the catheter protrudes from the proximal end of the elongate collection bag neck and the sleeve. The frustoconically-shaped distal end 22 of the catheter has a greater diameter than the inner diameter 45 of the sleeve, thereby preventing the catheter from being dislodged from the collection bag neck as the collection bag body fills with urine.

The retaining ring 60 may then be placed over the proximal end of the catheter 20. The retaining ring has a catheter pathway 66 having a diameter that is substantially the same as the outer diameter of the catheter, so that the retaining ring frictionally engages the catheter. The distal end 52 of the introducer tip 48 may be placed over the catheter, the proximal end 36 of the elongate collection bag neck, the retaining ring 60, and the tubular sleeve 42. As previously discussed, the introducer tip may be formed of a soft, polymeric material, such as silicone, having an inner diameter 57 that is slightly larger than the outer diameter 43 of the sleeve. The introducer tip 48 may be somewhat flexible and may secure the elongate collection bag neck 30 to the sleeve. The introducer tip may also restrict the movement of the retaining ring.

The open distal end 38 of the elongate collection bag neck may then be sealed to the opening 79 in the proximal end 78 of the collection bag body 70, so that the collection bag neck conduit 31 of the elongate collection bag neck and the interior of the collection bag body are in sealed, fluid communication with each other. Thus, the catheter 20 is in sealed fluid communication with the elongate collection bag neck 30 and the collection bag body 70.

In another aspect, a protective cap 90, as illustrated in FIG. 2, may be configured to fit over the introducer tip 48 to prevent contamination of the catheter 20 and maintain sterile conditions prior to catheterization. In one aspect, the protective cap may be formed of a thermoplastic material. When the cap is in place, the urinary catheter within the collection bag neck remains sterile. When the cap is removed, the portion of the urinary catheter disposed therein the elongate collection bag neck is fluidically and environmentally sealed within the elongate collection bag neck, permitting ingress into the urinary catheter collection bag substantially exclusively via the inner lumen of the urinary catheter.

In order to use the urinary catheter collection system of the present invention, a user removes the protective cap, and with one hand holds the sleeve 42 of the guide housing 40 between the walls 32, 33 of the elongate collection bag neck 30. With the other hand, the user grips the catheter 20 between the walls of the elongate collection bag neck and urges the catheter towards the proximal end 36 of the collection bag neck. This action causes the elongate collection bag neck walls to collapse longitudinally, producing accordion-like folds as the collection bag neck distal end 38 approaches the guide housing. The user then returns the elongate collection bag neck 30 to its original unfolded condition. The proximal end 24 of the catheter is inserted into the urethra, and the process is repeated until the proximal end of the catheter has passed through the urethra and reaches the bladder.

As previously discussed, in one aspect, the optional retaining ring 60 frictionally engages the catheter 20. The catheter, however, may easily slide longitudinally through the retaining ring when the catheter is being urged towards the proximal end 36 of the elongate collection bag neck. If the user attempts to return the extended catheter to the elongate collection bag neck, whether intentionally or unintentionally, the retaining ring 60 will engage the shoulder 46 on the interior of the sleeve 42. As illustrated in FIG. 4, because only one side of the retaining ring engages the shoulder, the retaining ring will not be axially aligned with the catheter, and the at least one retaining tab 64 of the retaining ring will more forcefully engage the catheter, preventing the catheter 20 from sliding longitudinally back into the elongate collection bag neck 30.

Figure 8:
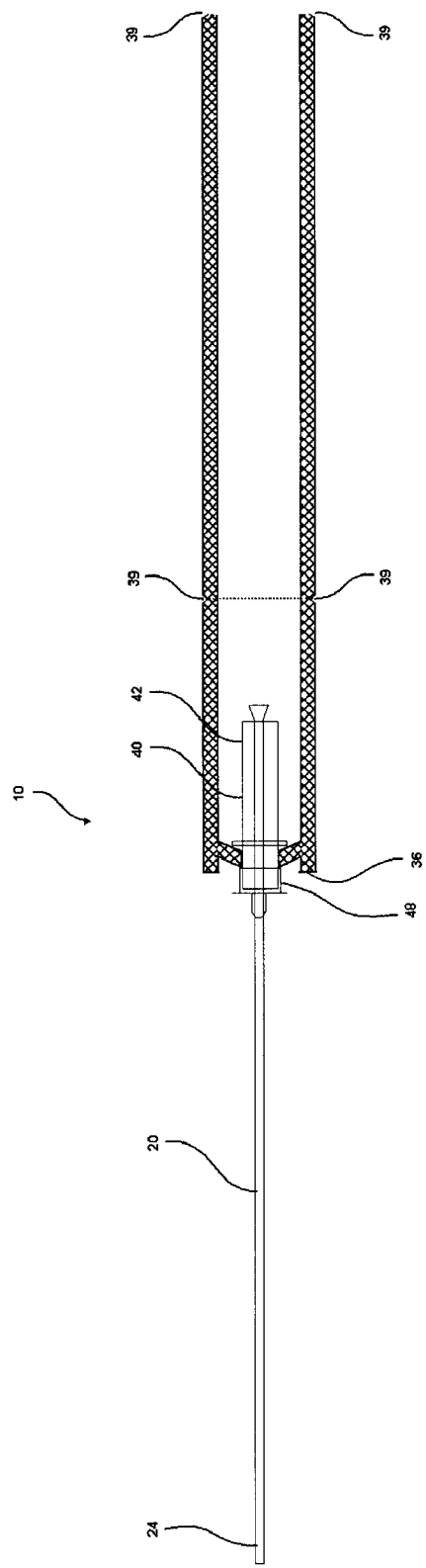
FIG. 8 is a top view of one embodiment of the urinary catheter collection system of the present invention showing the catheter in an extended position and the collection bag body removed from the catheter collection system.

The catheterized user may elect to allow urine to flow from the catheter through the elongate collection bag neck 30 into the collection bag body 70. Prior to use, the catheter user may, however, elect to tear the elongate collection bag neck at the at least one perforation 39 near the distal end 38 of the collection bag neck, as illustrated in FIG. 8, so that the contents of the collection bag body may be poured into a suitable receptacle, such as a toilet. The catheterized user may, however, elect to tear the elongate collection bag neck at the at least one perforation 39 located in an intermediate portion of the elongate collection bag neck, thus separating the collection bag body 70 from the rest of the urinary catheter collection system 10. In this instance, urine will flow from the catheter through the elongate collection bag neck 30, out the opening created where the elongate collection bag neck was torn, and into a suitable receptacle. The user, in this instance, will avoid the step of emptying the used collection bag body, which eliminates the possibility of urine spillage during the emptying process. Additionally, if the user is in a wheelchair, this would allow the user to remain in the wheelchair and direct the urine, via the collection bag neck, into the receptacle.

Although several embodiments of the invention have been disclosed in the foregoing specification, it is understood by those skilled in the art that many modifications and other embodiments of the invention will come to mind to which the invention pertains, having the benefit of the teaching presented in the foregoing description and associated drawings. It is thus understood that the invention is not limited to the specific embodiments disclosed herein above, and that many modifications and other embodiments are intended to be included within the scope of the appended claims.

Moreover, although specific terms are employed herein, as well as in the claims which follow, they are used only in a generic and descriptive sense, and not for the purposes of limiting the described invention, nor the claims which follow.

What is claimed is:

1. A urinary catheter collection bag for use with a urinary catheter having an inner lumen, the urinary catheter collection bag comprising:
    an elongate collection bag neck defining a neck conduit configured for receipt of the urinary catheter, wherein the entire urinary catheter is disposed within the elongate collection back neck; and
    a collection bag body in selective sealed fluid communication with the elongate collection bag neck and defining an interior volume, wherein a transition area between the collection bag body and the elongate collection bag neck is at least partially perforated such that the collection bag body is selectively detachable from the elongate collection bag neck, and wherein the collection bag is configured to permit a user to selectively detach the collection bag body prior to using the catheter, thus permitting urine from the user's body to flow therethrough the collection bag neck and directly into a receptacle, without the need for the collection bag body.

2. The urinary catheter collection bag of claim 1, wherein the collection bag is configured to permit a user to be catheterized, and while catheterized, permit urine from the user's body to flow therethrough the collection bag neck and into the collection bag body for subsequent disposal.

3. The urinary catheter collection bag of claim 1, wherein the collection bag body is selectively detachable from the elongate collection bag neck at a distal end portion of the collection bag neck.

4. The urinary catheter collection bag of claim 1, wherein the elongate collection bag neck has a longitudinal axis and wherein an intermediate portion of the elongate collection bag neck is configured to selectively separate, thereby substantially bisecting the elongate collection bag neck in a direction substantially transverse to its longitudinal axis.

5. The urinary catheter collection bag of claim 1, further comprising a guide housing having a proximal end and a distal end fixedly attached to a proximal end of the elongate collection bag neck and defining a longitudinally extending catheter pathway, wherein the catheter is configured to slide longitudinally therethrough the catheter pathway, and wherein the guide housing is configured to allow a user to selectively slide the catheter in a first direction therethrough the guide housing pathway.

6. The urinary catheter collection bag of claim 1, wherein the distal portion of the catheter is frustoconically shaped in order to prevent the distal end of the catheter from being removed therethrough the guide housing.

7. The urinary catheter collection bag of claim 5, wherein a protective cap is selectively detachable from the guide housing.

8. The urinary catheter collection bag of claim 7, further comprising a retaining ring configured to prevent the catheter from moving in a second longitudinal direction therethrough the guide housing pathway.

9. The urinary catheter collection bag of claim 1, wherein the catheter is lubricated.

10. The urinary catheter collection bag of claim 1, wherein the elongate collection bag neck and collection bag body are comprised of a thermoplastic material.

11. The urinary catheter collection bag of claim 10, wherein the thermoplastic material is substantially transparent.

12. The urinary catheter collection bag of claim 10, wherein the thermoplastic material is substantially opaque.

13. The urinary catheter collection bag of claim 10, wherein volume indicia are provided on a portion of the collection bag body.

14. A urinary catheter collection system comprising:
an elongate urinary catheter having an inner lumen;
an elongate collection bag neck defining a neck conduit configured for receipt of the urinary catheter, wherein the entire urinary catheter is disposed within the elongate collection back neck; and
a collection bag body in selective sealed fluid communication with the elongate collection bag neck and defining an interior volume, wherein a transition area between the collection bag body and the elongate collection bag neck is at least partially perforated such that the collection bag body is selectively detachable from the elongate collection bag neck, and wherein the collection bag is configured to permit a user to selectively detach the collection bag body prior to using the catheter, thus permitting urine from the user's body to flow therethrough the collection bag neck and directly into a receptacle, without the need for the collection bag body.

15. The urinary catheter collection bag of claim 14, wherein the collection bag is configured to permit a user to be catheterized, and while catheterized, permit urine from the user's body to flow therethrough the collection bag neck and into the collection bag body for subsequent disposal.

16. The urinary catheter collection system of claim 14, wherein the collection bag body is selectively detachable from the elongate collection bag neck at a distal end portion of the collection bag neck.

17. The urinary catheter collection system of claim 14, wherein the elongate collection bag neck has a longitudinal axis and wherein an intermediate portion of the elongate collection bag neck is configured to selectively separate, thereby substantially bisecting the elongate collection bag neck in a direction substantially transverse to its longitudinal axis.

* * * * *